(12) United States Patent
Sime et al.

(10) Patent No.: US 9,386,684 B2
(45) Date of Patent: Jul. 5, 2016

(54) PHYSICAL CONTACT LAYER FOR BODY-WORN LEADWARE USING SELECTIVE DEPOSITION

(71) Applicant: Molex, LLC, Lisle, IL (US)

(72) Inventors: David G. Sime, Minnetonka, MN (US); Richard Koble, Mankato, MN (US)

(73) Assignee: Molex, LLC, Lisle, IL (US)

( * ) Notice: Subject to any disclaimer, the term of this patent is extended or adjusted under 35 U.S.C. 154(b) by 451 days.

(21) Appl. No.: 13/804,949

(22) Filed: Mar. 14, 2013

(65) Prior Publication Data

US 2013/0248226 A1     Sep. 26, 2013

Related U.S. Application Data

(60) Provisional application No. 61/613,067, filed on Mar. 20, 2012.

(51) Int. Cl.
| | |
|---|---|
| H05K 1/09 | (2006.01) |
| H05K 1/02 | (2006.01) |
| A61B 5/0408 | (2006.01) |
| A61N 1/04 | (2006.01) |
| A61B 5/00 | (2006.01) |
| H05K 1/03 | (2006.01) |

(52) U.S. Cl.
CPC .............. *H05K 1/02* (2013.01); *A61B 5/04085* (2013.01); *A61N 1/0484* (2013.01); *H05K 1/0393* (2013.01); *A61B 5/6805* (2013.01); *A61B 2562/125* (2013.01); *A61B 2562/164* (2013.01); *H05K 1/038* (2013.01); *Y10T 156/10* (2015.01)

(58) Field of Classification Search
CPC ....... H05K 1/02; H05K 1/038; H05K 1/0393; A61N 1/0484; A61B 2562/125; A61B 2562/164

USPC .......................................................... 174/251
See application file for complete search history.

(56) References Cited

U.S. PATENT DOCUMENTS

| | | | | |
|---|---|---|---|---|
| 5,012,810 A | * | 5/1991 | Strand ................ | A61B 5/04087 600/391 |
| 5,215,087 A | * | 6/1993 | Anderson .......... | A61B 5/04087 600/392 |
| 5,505,200 A | * | 4/1996 | Takaki ............... | A61B 5/04087 600/395 |
| 5,763,058 A | | 6/1998 | Isen | |
| 5,813,981 A | * | 9/1998 | Carim ................. | A61B 5/0408 600/372 |

(Continued)

OTHER PUBLICATIONS

Application No. PCT/US2013/032991, filed Mar. 19, 2013, *Notification Concerning Transmittal of International Preliminary Report on Patentability*, mailed Oct. 2, 2014, 7 pages.

(Continued)

*Primary Examiner* — Sherman Ng
(74) *Attorney, Agent, or Firm* — James A. O'Malley (57) ABSTRACT

A printed electrical circuit and methods for additively printing electrical circuits. Patterned layers of conductive, insulating, semi-conductive materials, and other materials are print deposited on a flexible or rigid substrate to form electrical circuits. A buffering layer is selectively deposited to cover or encapsulate these materials to comprise a comfort layer that provides a soft and comfortable interface to the skin of a wearer. The comfort layer can be selectively deposited on the same press that the conductive, insulating, semi-conductive materials, and other materials are deposited. Further, the comfort layer is selectively deposited only where it is desired and exactly where it is desired.

33 Claims, 8 Drawing Sheets

(56) References Cited

U.S. PATENT DOCUMENTS

| | | | |
|---|---|---|---|
| 2002/0137999 A1 | 9/2002 | Bandeian | |
| 2005/0251003 A1* | 11/2005 | Istvan | A61B 5/0006 |
| | | | 600/393 |
| 2007/0038057 A1* | 2/2007 | Nam | A61B 5/6805 |
| | | | 600/388 |
| 2008/0135408 A1 | 6/2008 | Sjolander | |
| 2009/0088652 A1* | 4/2009 | Tremblay | A41D 13/1281 |
| | | | 600/388 |
| 2010/0140673 A1 | 6/2010 | Daniel | |
| 2010/0198038 A1 | 8/2010 | Nagata | |
| 2010/0206614 A1 | 8/2010 | Park | |
| 2011/0190615 A1 | 8/2011 | Phillips | |

OTHER PUBLICATIONS

Numakura, Dominique, *Advanced Screen Printing—Practical Approaches for Printable and Flexible Electronics*, DKN Research, Haverhill MA, Sep. 2009, 8 pages.

Notification of Transmittal of the International Search Report and the Written Opinion of the International Searching Authority or the Declaration, International Application No. PCT/US2013/032991, mailed Jun. 10, 2013, 9 pages.

* cited by examiner

PHYSICAL CONTACT LAYER FOR BODY-WORN LEADWARE USING SELECTIVE DEPOSITION

RELATED APPLICATION

The present application claims the benefit of U.S. Provisional Application No. 61/613,067 filed Mar. 20, 2012, which is incorporated herein in its entirety by reference.

TECHNICAL FIELD

The invention relates generally to flexible electronics, and more particularly, to protective layers for printed flexible electronics, such as those used in body-worn leadware.

BACKGROUND

Flexographic, lithographic, gravure, screen printing, digital printing such as inkjet or drop on demand, and other processes, including those in which a central impression cylinder is used, are known in the art for printing a wide variety of articles. Recently, these and other processes and techniques have been used to print functional materials, including those required to make electrical circuits. Whereas etching and other subtractive processes for creating circuits are wasteful, relatively costly, and time-consuming, thereby limiting applicability and use, printing processes, by virtue of being additive, can be comparatively economical, efficient in the use of resources, and highly effective in meeting sufficient product quality standards, i.e., resolution, registration, and other indicators, for many applications. Resultant printed or otherwise selectively deposited products are therefore more attractive for a range of applications and industries, and especially where performance standards associated with the more mature silicon technologies do not necessarily need to be met.

Early circuit boards or base substrates used in the printing of electrical circuits, utilized insulating layers made of rigid fiberglass-reinforced resin or ceramic material. However, many printed circuit boards in use today employ flexible substrates, typically made of a polyester or polyimide material. Not only can conductive traces (wiring) be printed using known methods, but passive components (resistors, capacitors, inducers) and active components (transistors such as OFETs, switches, amplifiers, filters, electric batteries, memory, logic devices) are also known in the art. As a result, intricate electrical circuits that are printed on flexible substrates can comprise printed flexible electronics.

The aforementioned printed flexible electronics can be used in body-worn leadware. For example, as part of an electrocardiogram (ECG) procedure, a medical professional may attach electrodes to a patient and connect those electrodes to recording devices using wire leads. Leads often comprise individual wires that require considerable management to avoid becoming entangled in other devices or caught in clothing, bedding, or other equipment. Lead wires can sometimes be arranged or organized into a "harness" which keeps the wires together and more manageable. However, this lead wire harness can further complicate instances where individual leads need to be broken out to make particular connections to individual sensing points. Alternatively, the interconnection between electrodes on a patient and the recording device can be made using a device in which a conductive path is constructed (often printed) on a thin, flat substrate which can lie flatter on the patient. Such devices fall into the category known as "leadware" and provide effectively a "wearable" set of ECG lead wires to the patient. These body-worn leads can be affixed to the appropriate locations and electrodes on the patient, where they remain affixed to the patient and configured to sense ECG data. This saves the medical professional from having to constantly manage lead wires. It is also possible that the electrodes can be constructed to be integral with the leadware. Body-worn leadware is useful in myriad other applications, for example, wherever it may be desirable to measure patient vital signs or other physical characteristics, including respiration monitoring, x-rays, C.A.T. scans, fluoroscopy, and so on. Other applications for leadware can include devices for electro-stimulation for various types of continuous or intermittent diagnoses or therapies.

However, because body-worn leadware is in contact with the patient's skin, it can be uncomfortable for the wearer or can cause irritation, chafing, or scratching of the wearer's skin. The substrates, conductive layers, and dielectric layers that comprise traditional leads contain components with various organic or inorganic materials that are designed for a conductive, insulating, or semi-conductive purpose and are not necessarily designed to be comfortable to the user. Indeed they have a stiffness and sharpness of edge which, just as with paper, can lead to cuts and abrasions. Therefore, body-worn diagnostic or therapeutic devices typically require some sort of comfort layer to protect the skin of the wearer from the leadware in order to be comfortable.

Some body-worn leads have incorporated protective layers onto the printed electronically functional layers. Typically, this is achieved by the lamination of a "comfort layer" made of a woven or non-woven, spun fabric. However, traditional comfort layers suffer from problems in manufacturing, distribution, and use.

For example, the lamination of a traditional comfort layer typically requires that the comfort layer material first be coated with an adhesive and then laminated to the substrate of the flexible product. This lamination often must be carried out in register so that features of the flexible electronics themselves can be aligned with the corresponding and appropriate cut-outs in the comfort layer material. Thus, the lamination process often requires at least a secondary processing step on at least a secondary piece of equipment. Also, the secondary piece of equipment must have enough sophistication to support the necessary registration of the two layers.

Further, there is often considerable waste of the comfort layer material because the traditional comfort layer manufacturing process typically starts with a whole web or sheet (100% coverage) of material which is die cut before lamination, and then die cut along with the final printed circuit when the assembly is singulated. This is done because the various intricately-aligned features of the printed electronics can be difficult to align with the corresponding features in a pre-cut piece of comfort layer material. The fraction of comfort layer material used in the final printed circuit product is far less than 100%. Therefore, not only are additional steps incurred, thus increasing production cost, but comfort layer material is applied, then cut away and discarded during production, thus further increasing material costs.

Figure 1A:
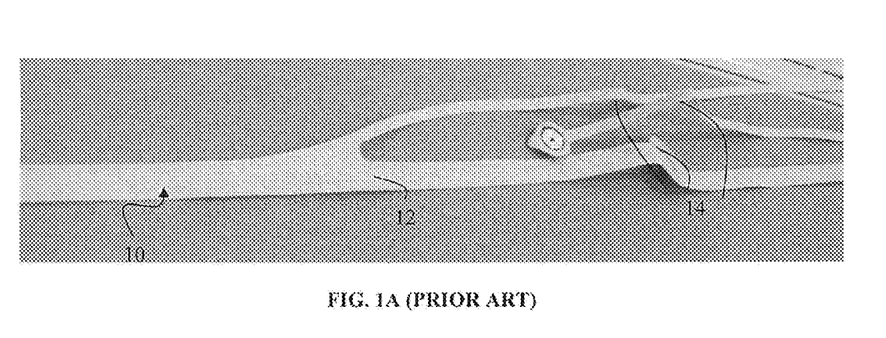
FIG. 1A depicts a flexible printed electronic part of the prior art having a traditional comfort layer wherein the part has retained a memory fold.
Figure 1B:
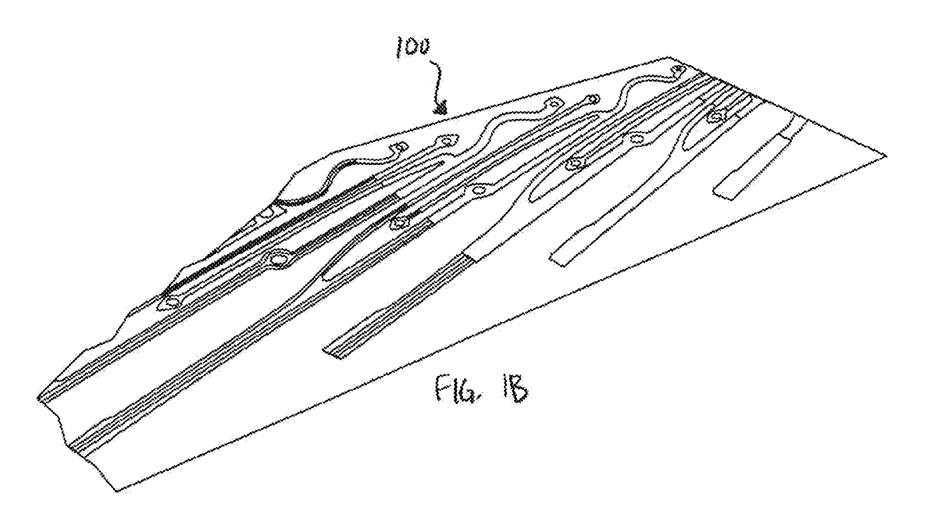
FIGS. 1B and 2 depict a section of a web of parts covered in dielectric and partially in a comfort layer, according to an embodiment.
Figure 2:
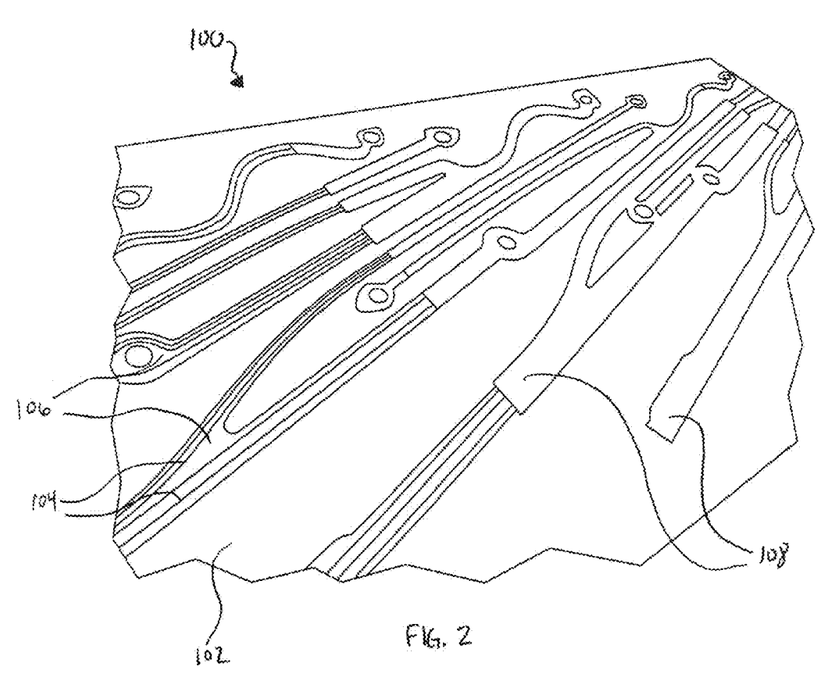

Additionally, the packaging of traditional printed flexible electronics incorporating a comfort layer is problematic. For use with adult patients, leadware can exceed a length of 36" long. In order to contain the leadware in packaging for distribution, typically, the product is folded over a stiffener or rolled on a spool. The rolled or folded unit and holder card or spool are then placed in a container for shipping. The conventional structure of leadware that includes a comfort layer with adhesive is such that a memory is formed, within the structure, of folds, creases, or rolls as the adhesive layer accommodates the stresses associated with any bending. As a result, bending during the packaging impresses a "kink" which the part retains throughout its useful life. For example, referring to FIG. 1A of the prior art, a flexible printed electronic part 10 of the prior art having a traditional comfort layer 12 is depicted after being unpackaged. Memory folds 14 are present in the part 10 where it was folded over its packaging insert card, even after unpacking. These memory folds can be problematic during use of the leadware. It can make the leads difficult to affix (and remain affixed) to the patient. Memory folds can also lead to more interference between the leadware and items in the vicinity such as clothing, bedding, etc. Likewise, there may be interference with the measurement of the patient's clinical information.

Therefore, there is a need for a comfort layer that can be prepared on flexible substrates and specifically, flexible printed electronics, that is easily, economically, and efficiently produced, that further does not suffer from memory fold retention problems of the prior art and can thus be easily packaged and used. Embodiments having such a comfort layer will allow more variety in packaging options, thereby adding value to its use.

SUMMARY

Embodiments of the present application substantially meet the aforementioned needs of the industry. In embodiments, patterned layers of conductive, insulating, semi-conductive materials, and other materials are deposited on a flexible substrate to form electrical circuits. A physical buffering layer is deposited on top of these materials to form a comfort layer. The construction is such that the comfort layer, regardless of its order in manufacturing is the layer which is closest to the patient or wearer when the device is deployed. The electrical circuits or circuitry so formed of single or multiple printed or otherwise additively deposited layers can comprise or compose transistor devices, including organic thin film transistors (OTFTs or OFETs), multiple transistor circuits or assemblies, or other electrical devices, for example batteries, sensors, displays, memory arrays, antennas, and the like. The comfort layer can be configured to cover or encapsulate some or all of these devices as needed to provide a soft and comfortable interface to the skin.

In embodiments, a comfort layer can comprise ink having a soft, open texture similar to that of woven or unwoven fabrics. In embodiments, the comfort layer can comprise an expanding plasticised or "puff ink" that can stand alone or comprise an additive to plastisol inks. In an embodiment, plastisol puff inks can comprise suspended PVC particles in a plasticizer, such as an ester, and a puff additive. The plastisol puff ink that flows as a liquid or ink for purposes of deposition, and expands upon curing or the application of heat. In certain embodiments, the plasticizer is an ester of polycarboxylic acid with linear or branched aliphatic alcohols of moderate chain length. In a particular embodiment, the plasticizer comprises a phthalate ester of straight-chain or branched-chain alkyl alcohol.

In embodiments, plastisol puff inks sit atop the substrate and patterned layers of conductive, insulating, and semi-conductive materials but do not soak into them, instead covering or encapsulating the patterned layer materials. In other embodiments, the comfort layer can comprise silicone, urethane, cellulosic, fibrous or other soft and non-abrasive materials selectively deposited.

In a feature and advantage of embodiments of the invention, a puff ink comfort layer can be processed in-line with other steps of selective deposition of materials during production. When compared to comfort layer production of the prior art, multiple process steps are saved. First, the removal of the substrate from the system, such as a printing press, which is used to achieve the selective deposition of the layers other than the comfort layer, is no longer required. The comfort layer can be selectively deposited on the same press that the conductive, insulating, semi-conductive materials, and other materials are deposited. Second, no adhesive layer is required to first be coated to the comfort layer material or to the underlying layers prior to the placement or deposition of the comfort layer on the substrate and conductive, insulating, and semi-conductive components. Third, no intricate cuts of the comfort layer material prior to installation on the substrate or in concurrence with the final printed circuit cut are required and thus no tight registration of the comfort layer to the underlying pieces is required. Therefore, manufacturing time is saved compared to comfort layer production of the prior art.

In another feature and advantage of embodiments of the invention, a puff ink comfort layer is selectively deposited only where it is desired and exactly where it is desired, by, for example, printing, spray coating, screen printing or coating, coating through a patterned or otherwise previously prepare mask, or other techniques. When compared to comfort layer production of the prior art, material cost is saved. The waste incurred in cutting a larger than required sheet of material and scrapping the unused part is avoided. On the contrary, the comfort layer is deposited in the precise amount and in the precise location as is desired in the final printed flexible electronics, with due allowance for manufacturing tolerance. Thus, material cost is saved compared to comfort layer production of the prior art.

In another feature and advantage of embodiments of the invention, a puff ink (or other) comfort layer can comprise certain dielectric properties. In embodiments, material and production costs can therefore be additionally reduced by using the puff ink comfort layer as a replacement for certain traditional dielectric layers, when compared to flexible printed electronics of the prior art. In embodiments, material costs are saved due to the dual role of the single comfort layer in embodiments of a particular application of a printed circuit; the separate dielectric layer materials are no longer required to be printed into the circuit. Production costs are likewise saved due to the dual role; the dielectric layer is now superfluous and no longer needs to be printed into the circuit. In embodiments where a dielectric layer is used with a puff ink comfort layer, embodiments of the puff ink comfort layer add to the insulation properties of the overall circuit.

In another feature and advantage of embodiments of the invention, a puff ink comfort layer comprises a waterproof barrier. In other embodiments, a puff ink comfort layer can be deposited on a heavy waterproofing layer to create a waterproof barrier that is still a soft and comfortable interface to the skin. As a result, the flexible printed electronics of embodiments can be used in water-laden environments. For example, embodiments of body-worn leads can be utilized in diagnostic or therapeutic devices worn in swimming pool testing or scuba diving applications. Additionally, in dry environments where liquid has a chance of contacting the printed electronics, embodiments of the flexible printed electronics are further protected from water damage by the waterproof barrier provided by embodiments of the comfort layer.

In another feature and advantage of embodiments of the invention, no memory fold is retained in the electronics after crimping or bending. As a result, body-worn leads are more easily affixed to a patient, and are more likely to remain affixed than the body-worn leads of the prior art. Additionally, the underlying electronics are not stressed or damaged by any permanent memory of a fold retained by the comfort layer, and measurement characteristics are more likely to be measured accurately than the body-worn leads of the prior art.

Because no memory fold exists in embodiments, myriad options for packaging embodiments of the printed flexible electronics are available. For example, embodiments can be rolled up or folded. As a result, the formatting of the packaging can be made to suit widely accepted and broadly used packaging, handling, and distribution methods, including those traditionally recognized in a medical environment. As a result, packaging and handling costs are reduced as no intermediary card insert is required, compared to packaging in the prior art. And further, the body-worn leads comprising embodiments of the printed flexible electronics allow handing in packaging more familiar and convenient to medical professionals and other end users.

Embodiments of the present application are not limited to medical applications. On the contrary, embodiments can be utilized, for example, in the context of "smart clothes" having electronics embedded within a piece of clothing for novelty or utility, or wearable computers, or any other application where electronics worn against the body necessitate a comfort layer between the electronic components and the wearer. For example, performance monitoring for humans and animals in stressful (combat or emergency) or competitive (sports) situations can also call for distributed sensing and collection of data. In addition, the expanded use of personal electronic devices for information and entertainment purposes will benefit from clothing attached leadware made more convenient with an efficiently generated comfort layer. More generally, the integration of electronic functionality with other uses of textiles, such as hospital gowns, blankets, tents, mattress covers, or pillow covers, for example, all benefit from the use of an economically constructed comfort layer to protect the user.

Selective deposition methodologies or techniques utilized in various embodiments can include, for example, any form of additive printing techniques including, but not limited to, gravure, waterless offset, direct image waterless offset, dry offset, lithographic, intaglio, embossing, engraving, screen, rotary screen, silkscreen, letterpress, flatbed, digital printing such as ink jetting and drop on demand techniques, xerographic techniques, flexographic, aerosol, pad, dip-pen, or any other related printing techniques or combinations thereof. In embodiments, the printing methodology or technique chosen can be based on the particular substrate, or similarly, the particular electric or dielectric layers desired. In other embodiment, selective deposition methodologies can comprise, for example, spray coating, screen coating, coating through a patterned or otherwise previously prepare mask, or other techniques.

The above summary of the invention is not intended to describe each illustrated embodiment or every implementation of the present invention. The figures and the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Referring generally to FIGS. 1B, 2 and 3A-3C, a set of flexible printed electronics 100 according to an embodiment are depicted. The set of flexible printed electronics 100 generally comprise individual circuit traces each having a substrate 102, a conductive layer 104, a dielectric layer 106, and a comfort layer 108. Of course, any particular embodiment can comprise greater or fewer layers, as the below-described embodiments are for illustration purposes only and are in no way limiting.

Substrate 102 comprises the base material onto which the conductive, non-conductive, and comfort components will be printed. Substrate 102 can be any suitable substrate in a sheet, roll, web, or similar structure. In an embodiment, substrate 102 comprises a fabric layer, such as cotton or polyester, woven, or non-woven. In other embodiments, substrate 102 comprises other flexible substrates such as polymer film such as polyethylene terephthalate film (PET), Polyethylene naphthalate (PEN), polyimide foil (PI), polypropylene, polyethylene, polystyrene, or any of a variety of polymer films or combinations thereof. In other embodiments, substrate 102 comprises flexible foil, film, paper, metalized film, or coatings, laminates, and combinations thereof. In still other embodiments, substrate 102 can comprise rigid substrates such as glass, silicon, or epoxy resin. Other suitable substances are also considered, depending on the application of a particular embodiment, and the properties of a particular substrate 102. Substrate 102 can be configured to be cut into the desired final shape prior to the printing or depositing of other layers, or can comprise a sheet or web onto which the conductive, non-conductive, and comfort components are to be printed for later cutting.

In still other embodiments, a discrete substrate 102 is not included in the set of flexible printed electronics 100. Instead, in such embodiments, one of the other layers, such as conductive layer 104 or dielectric layer 106, or another layer formed also through selective deposition, acts as the base layer onto which the conductive, non-conductive, and comfort components are be printed.

Conductive layer 104 comprises an electrically functional electronic ink, toner, or other coating or material that is deposited or printed on substrate 102. In embodiments, electrically functional electronic inks are available from Henkel Corporation or DuPont Inc., for example. In embodiments, conductive layer 104 can be made of any conductive material, such as for example, but not limited to, silver, platinum, palladium, copper, nickel, gold, or aluminum or conductive polymer. Therefore, the leads are configured to enable the flow of electricity through conductive layer 104. In other embodiments, there can be more than one conductive layer 104, effectively isolated from other conductive layers 104 by one or more insulating dielectric layer 106. Conductive layer 104 can be deposited in any shape or configuration, for example, straight or rounded, or with any number of sequences of curves or straight sections, in embodiments.

Dielectric layer 106 comprises an insulating layer that covers or encapsulates the first layer of conductive traces of conductive layer 104. In embodiments, dielectric layer 106 can be made of any insulating or non-conductive material or coating, such as for example, but not limited to, organic or inorganic insulators such as, for example, vinyl or urethane resins and binders such as those provided by Henkel Corporation or DuPont Inc. Therefore, dielectric layer 106 is configured such that electricity does not flow through the material of dielectric layer 106. Dielectric layer 106 can be deposited similarly to conductive layer 104, in any shape or configuration, for example, straight or rounded, or with any number of sequences of curves or straight sections, in embodiments.

In embodiments, the aforementioned layers 102, 104, and 106 can create active and passive electronic devices. Patterned layers therefore can comprise conductive, semiconductive, and insulating materials printed with suitably formulated conductive, insulating, or semiconductive ink, fluid, powder, particulate, or other deposition compositions. In other embodiments, the aforementioned layers 102, 104, and 106 can create organic thin film transistors (OTFTs). As is known to those skilled in the art, transistor devices in general comprise source and drain, semiconductor, dielectric, and gate layers. Patterned layers therefore can comprise conductive, semiconductive, and insulating materials printed with suitably formulated conductive, insulating, or semiconductive ink, fluid, powder, particulate, or other deposition compositions. In an OTFT, the semiconductor layer can comprise an organic material, for example a polymer. Transistors and OTFTs can be used to form radio frequency identification (RFID) circuits or "tags," passive or active "smart labels," batteries, displays and drivers, and other devices or combinations thereof. In other embodiments, sensors or monitoring electronics, signal conditioning, or electro-stimulation devices such as those described above in the medical context are created.

Comfort layer 108 comprises a soft, sponge- or fabric-like expanded layer that covers or encapsulates dielectric layer 106, conductive layer 104, if so exposed, and portions of substrate 102, if so exposed. For example, referring to FIG. 3A, comfort layer 108 encapsulates dielectric layer 106. In another example, referring to FIG. 3B, comfort layer 108 encapsulates dielectric layer 106, portions of conductive layer 104, and portions of substrate 102. Other variations of encapsulations of dielectric layer 106, conductive layer 104, and substrate 102 by comfort layer 108 are also possible. Comfort layer 108 can be deposited similarly to conductive layer 104 and dielectric layer 106, in any shape or configuration, for example, straight or rounded, or with any number of sequences of curves or straight sections, in embodiments.

Figure 3A:
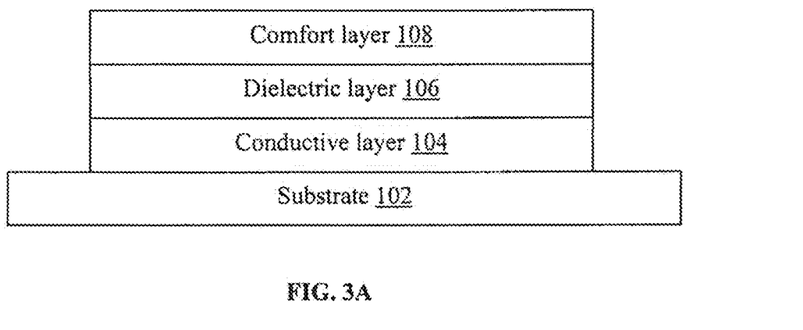
FIG. 3A is a cross-sectional block diagram of flexible printed electronics having a selectively deposited puff ink comfort layer, according to an embodiment.
Figure 3B:
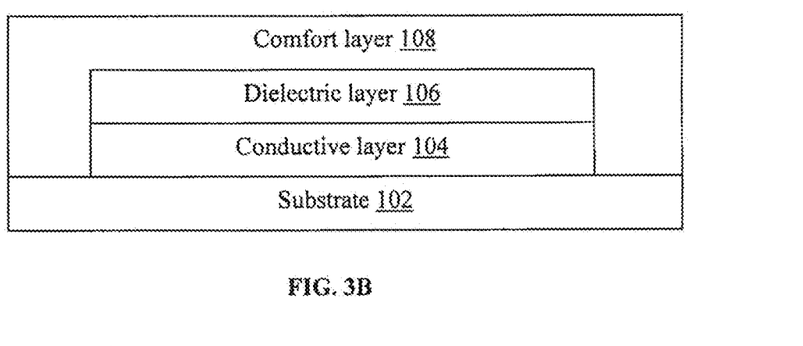
FIG. 3B is a cross-sectional block diagram of flexible printed electronics having a selectively deposited puff ink comfort layer, according to an embodiment.

Comfort layer 108 can be made of an expanding or puff ink. In embodiments, a puff additive to plastisol inks creates a plastisol puff ink that flows as a liquid but sets like a plastic, yet retains a soft sponge- or fabric-like compliant texture because it expands rapidly upon curing or because of the nature of the material. In embodiments, the soft sponge- or fabric-like, compliant and resilient texture of comfort layer 108 provides a soothing or comfortable interface to the skin of a wearer, when set of flexible printed electronics 100 is positioned proximate a wearer's skin or body. A raised or elevated effect of the puff ink comfort layer 108 creates additional comfort properties besides its soft, sponge-like texture. When positioned against the skin, comfort layer 108 thus provides additional spacing from any attached, complementary electronics or inadvertently exposed layers of substrate 102, conductive layer 104, or dielectric layer 106.

The layers 102, 104, 106, and 108 can comprise any dimension or size suitable for the particular embodiment or application. The possible shapes and configurations are limitless. Further, multiple layers of conductive layer 104, dielectric layer 106, and comfort layer 108 can be deposited or printed, in embodiments. In an alternative embodiment, one or more layers 104 or 106 are printed adjacent to, or in the same plane as, or side-by-side comfort layer 108. For example, if comfort layer 108 has insulative properties, in an embodiment, conductive layer 104 can be printed on substrate 102, and comfort layer 108 is printed alongside conductive layer 104 on substrate 102 and optionally over conductive layer 104. Upon curing, comfort layer 108 expands to encapsulate and insulate at least a portion of conductive layer 104.

Figure 3C:
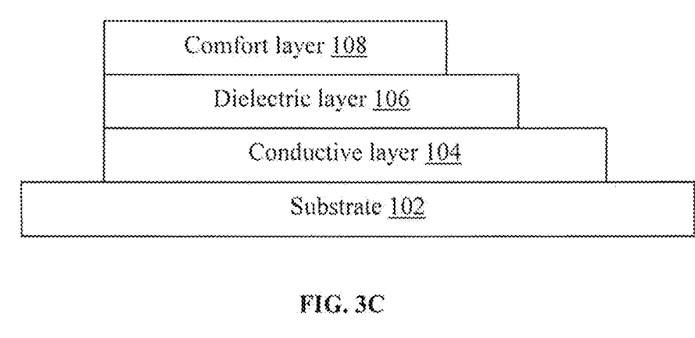
FIG. 3C is a cross-sectional block diagram of flexible printed electronics having a selectively deposited puff ink comfort layer, according to an embodiment.

Referring specifically to FIG. 3C, comfort layer 108 can be selectively deposited on dielectric layer 106 and conductive layer 104 so as to expose conductive layer 104. In embodiments, conductive layer 104 can be in electrical communication with other conductive elements where left exposed. For example, sensors or monitoring electronics, signal conditioning, electro-stimulation devices, or displays, as described above, can be electrically coupled to conductive layer 104 where exposed.

Figure 4:
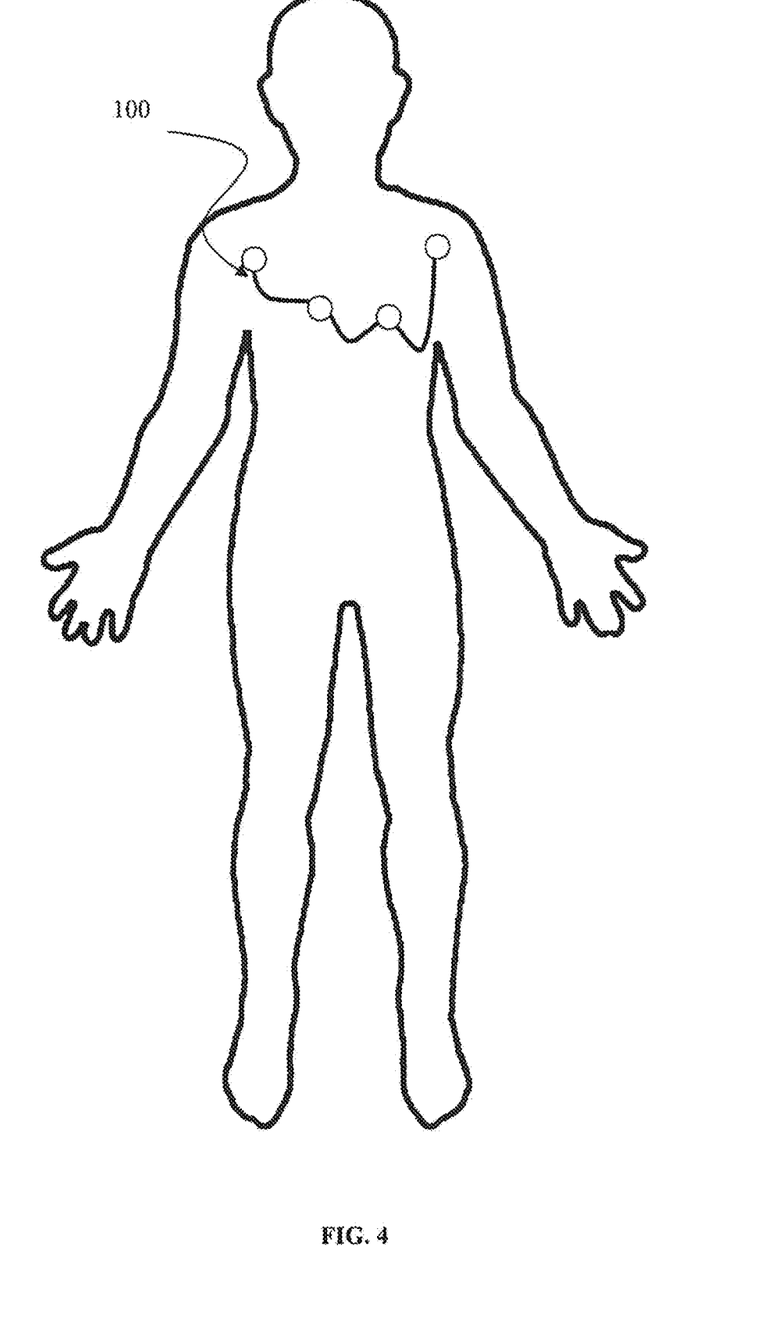
FIG. 4 depicts flexible printed electronics having a selectively deposited puff ink comfort layer coupled to a patient, according to an embodiment.

In operation, referring to FIG. 4, a set of flexible printed electronics 100 having a comfort layer 108 of puff ink can be attached to a patient. For example, in an ECG procedure, the set of flexible printed electronics 100 comprising a circuit made of substrate 102, conductive layer 104, and dielectric layer 106 is configured as body-worn leadware to measure patient body characteristics. A medical professional removes set 100 from its packaging, and positions set 100 with comfort layer 108 against the patient's skin. In embodiments, as desired, set 100 can be affixed or operably coupled to the patient such that the electrodes themselves are coupled to the patient, wherein the leadware hangs from the coupled electrodes. Other attachment or coupling schemes are also considered, such as by adhesive, applied pressure, or any other suitable device or method. Subsequently, an electrical current can be applied through set 100, and specifically, conductive layer 104, to electrically activate and operate set 100 as it is designed. Dielectric layer 106 provides proper insulation to conductive layer 104 to allow current to pass or not pass as appropriate. Because of the buffer of comfort layer 108 positioned between the skin of the patient and the conductive or insulating components of set 100, the patient remains comfortably attached to set 100.

Figure 5:
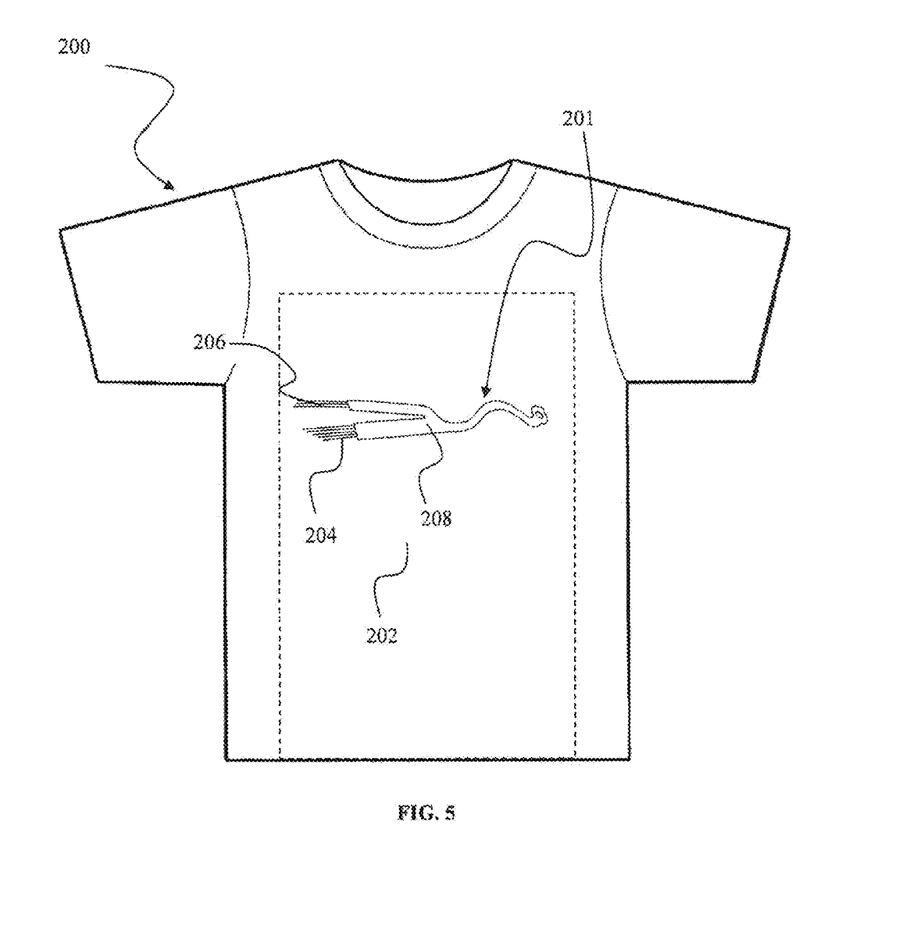
FIG. 5 depicts flexible printed electronics having a selectively deposited puff ink comfort layer installed into a piece of clothing, according to an embodiment.

Referring to FIG. 5, a set of flexible printed electronics having a puff ink comfort layer is configured within a piece of clothing 200, according to an embodiment. As shown, the clothing 200 is depicted as a T-shirt. However, embodiments are not limited to shirts, and may include pants, hats, shoes, gloves, or any other wearable item of clothing.

Clothing 200, as shown with a front section in cutout, includes a printed flexible circuit 201 placed along the back of the shirt. Similar to the printed flexible circuit described in previous embodiments, printed flexible circuit 201 includes a substrate 202, a conductive layer 204, a dielectric layer 206, and a comfort layer 208. As shown with the front section of clothing 200 cut away, the circuit is positioned such that comfort layer 208 interfaces with the skin of the wearer—specifically, the wearer's back. For ease of illustration, printed flexible circuit 201 is also shown with conductive layer 204 and dielectric layer 206 exposed beneath comfort layer 208. In embodiments, conductive layer 204 and dielectric layer 206 are not exposed to the wearer's skin.

The fabric of clothing 200 therefore provides substrate 202. Printed flexible circuit 201 can be incorporated into clothing 200 as a step intermediate the production of the shirt itself, or subsequent to the production of the shirt. In another embodiment, printed flexible circuit 201 is coupled to the fabric of clothing 200 via Velcro, sewn into the fabric, or otherwise subsequently attached. In such embodiments, substrate 202 comprises a base material onto which the conductive, non-conductive, and comfort components will be printed as in substrate 102. Substrate 202 can be any suitable substrate in a sheet, roll, web, or similar structure. In an embodiment, substrate 202 comprises a fabric layer, such as cotton or polyester, woven, or non-woven. In other embodiments, substrate 202 comprises other flexible substrates such as polymer film such as Polyethylene terephthalate-film (PET), Polyethylene naphthalate (PEN), polyimide foil (PI), polypropylene, polyethylene, polystyrene, or any of a variety of polymer films or combinations thereof. In other embodiments, substrate 202 comprises flexible foil, paper, metalized film, or coatings, laminates, and combinations thereof. In still other embodiments, substrate 102 can comprise rigid substrates such as glass, silicon, or epoxy resin.

Conductive layer 204 is printed or deposited onto substrate 202 at a location on substrate 202 where the sensor or circuit resulting from the printing process is useful for a particular purpose. For example, the circuit can be designed for monitoring nervous system signals, respiratory system signals, or circulatory system signals, for example. In another embodiment, the circuit can be designed for electrical stimulation.

Dielectric layer 206 is printed or deposited onto conductive layer 204 such that it covers or encapsulates all or portions of conductive layer 204 and, in embodiments, portions of substrate 202.

Comfort layer 208 is printed or deposited onto dielectric layer 206 such that it covers or encapsulates the patterned layer materials of conductive layer 204 and dielectric layer 206, and, in embodiments, portions of substrate 202. In an embodiment, comfort layer 208 comprises printed puff ink. Therefore, the printed flexible circuit 201 is buffered by comfort layer 208 where the wearer's skin contacts printed flexible circuit 201. The soft, sponge-like material that comprises comfort layer 208 provides an interface that is comfortable compared to the conductive and dielectric layers 204 and 206 printed beneath.

Additional printed flexible circuits 201 can similarly be incorporated onto substrate 202. Further, additional components can be operably coupled to printed flexible circuit(s) 201 in order to conduct electricity therethrough. For example, components can be coupled through the sleeve of clothing 200. Clothing 200 therefore provides a comfortable, readily wearable mechanism for incorporating flexible printed circuits 201 configured as medical devices. Clothing 200 can be donned by a patient prior to the running of various diagnostic or therapeutic tests where a monitor is desired along the patient's back. In another embodiment, a therapeutic electro-stimulation device can be applied to the patient's back. In other embodiments, the circuits provided by printed circuit 201 can be designed for novelty; for example, an interactive display through substrate 202.

In embodiments, printed flexible circuit 201 can be used in parallel with conductive threads sewn or woven into clothing 200, or, more particularly in embodiments, substrate 202. Conductive threads can be used for anti-static, electromagnetic shielding, data transfer, or heating purposes, or any other purpose inherent in conductive properties. In embodiments, conductive threads are configured to carry current for power and signals. Therefore, instead of discrete components coupling outside of clothing 200 to provide, for example, power or transmission conduit, such functionality can be incorporated into clothing 200 via conductive threads. The external components required to be coupled to clothing 200 to create a functional or enhanced circuit are therefore reduced, creating a readily wearable and freely moveable piece of clothing.

In an embodiment, a set of flexible printed electronics 100 can be packaged in a kit for shipping or storage. In embodiments, a kit is packaged for individual sale. In an embodiment, the set of flexible printed electronics 100 is folded over a stiffener or folded over itself and placed in kit packaging, such as a container or bag. In another embodiment, the set of flexible printed electronics 100 is rolled on a spool and placed in kit packaging. Due to the flexible resilient nature of the printed electronics and comfort layer, upon unpackaging or unrolling of the set 100, the set 100 is substantially free from memory folds. The packaged kit including set 100 can further include a set of instructions regarding application of the printed electronics 100, such as leadware, to a body, article of clothing, blanket, or the like. The instructions can include, for example, a map of a body, such as a human body, indicating placement of the printed electronics.

Figure 6:
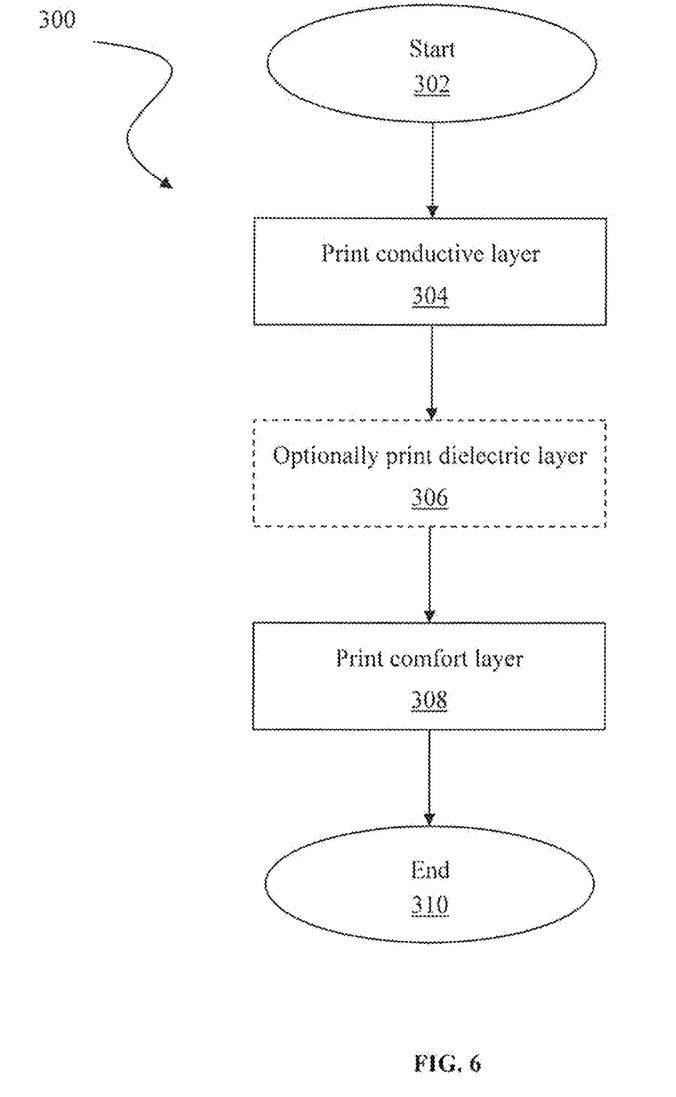
FIG. 6 depicts a method by which a flexible printed electronic having a selectively deposited puff ink comfort layer can be produced, according to an embodiment.

Referring to FIG. 6, a method 300 by which flexible printed electronics having a puff ink comfort layer can be produced is depicted, according to an embodiment. Beginning at step 302, the method is instantiated. Operationally, at step 302, the desired substrate 102 is positioned on a printing press system. Further, appropriate materials to create conductive layer 104, dielectric layer 106, and comfort layer 108 are assembled and incorporated into the printing press system, if appropriate.

At step 304, a conductive layer 104 is printed or deposited onto substrate 102, and is subsequently cured as needed depending on the material characteristics. Conductive layer 104 is printed such that current can flow through the circuit created by conductive layer 104 to form an appropriate electronic device, according to the desired embodiment.

At step 306, a dielectric layer 106 is printed or deposited onto conductive layer 104, and subsequently cured as needed depending on the material characteristics. Dielectric layer 106 is printed such that it covers or encapsulates all or portions of conductive layer 104 and, in embodiments, portions of substrate 102. In embodiments, portions of conductive layer 104 are left exposed where it is necessary to leave the conductive traces exposed in order to make electrical interconnection between the leadware and some other component. For example, dielectric layer 106 is not printed or deposed onto conductive layer 104 where conductive layer 104 is configured to interface with an electrode or recording device. In other embodiments, dielectric layer 106 is not printed, as depicted in FIG. 6, and comprises an optional printing step. In such embodiments, comfort layer 308 comprises certain dielectric properties and thereby acts in a dual role as both a dielectric layer and comfort layer.

Although a wide variety of inks and other materials can be used in printing conductive layer 104 and dielectric layer 106, conductive, insulating, or semiconductive patterned layers can be obtained, for example, by printing with a suitably formulated conductive, insulating, or semiconductive ink composition. Electrically conductive or semiconductive inks contain conductive or semi-conductive materials, such as conductive or semiconductive polymers or conductive or semiconductive metals or composites. Conductive materials containing metallic particles such as gold particles, silver particles, and like metallic particles, carbon particles, conductive or semiconductive polymers, composite particles, and like particles, or combinations thereof, can provide for the flow of electrons or electronic signals. The conductive metals or composites can be fine particulates or nanoparticulates. Intricate patterns can be printed with application-specific formulations, using, for example any form of gravure, flatbed, lithography, screen, rotary screen, digital printing, and like print methods, or combinations thereof.

At step 308, a comfort layer 108 is printed or deposited, and is subsequently cured as needed, onto dielectric layer 106 such that it covers or encapsulates the patterned layer materials of conductive layer 104 and dielectric layer 106, and, in embodiments, portions of substrate 102. In embodiments, portions of dielectric layer 106, portions of conductive layer 104, and/or portions of substrate 102 are left exposed in order to provide electrical contact and connection to, for example, the patient or to electrodes. In embodiments, the viscosity of comfort layer 108 can be adjusted to interface with particular printing press systems. For example, it may be useful for comfort layer 108 to have a lower viscosity on certain printing press systems in order to facilitate ease of printing, but have a higher viscosity on other printing press systems in order to facilitate ease of printing.

Printing methodologies or techniques utilized within the steps to print conductive layer 104 at step 304, print dielectric layer 106 at step 306, and print comfort layer 108 at step 308 can include, for example, any form of gravure, waterless offset, direct image waterless offset, dry offset, lithographic, intaglio, embossing, engraving, screen, rotary screen, silk-screen, letterpress, flatbed, digital printing such as ink jetting or drop on demand techniques, xerographic techniques, flexographic, aerosol, pad, dip-pen, or any other related printing techniques or combinations thereof. Each of the layers are cured upon deposition of each individual layer, and/or in batch form with an appropriate curing system, such as, for example, UV, IR, heat, ebeam, or the like, as appropriate with the ink or material composition used for the specific layer. In an embodiment, comfort layer 108 expands upon curing to encapsulate one or more of the other layers.

At step 310, the method 300 is concluded, except for the singulation of individual parts from the web or sheet on which they were printed. The newly created set of flexible printed electronics is removed from the printing press system. In embodiments, the set of flexible printed electronics can be placed individually or in groups in appropriate packaging.

Embodiments of circuits can comprise greater or fewer layers of substrate 102, conductive layer 104, dielectric layer 106, other functional layers, and comfort layer 108. As a result, method 300 can comprise greater or fewer steps, including iterations, of the aforementioned steps of printing or depositing conductive layer 104 onto substrate 102, printing or depositing dielectric layer 106 onto conductive layer 104, and printing or depositing comfort layer 108 onto dielectric layer 106.

In an alternative embodiment (not shown), an electric circuit assembly is formed in a reverse configuration. For example, a comfort layer material is selectively deposited on a first substrate, the substrate comprising a web or sheet having an optional release layer. The comfort layer is cured so that it expands to form a well-formed comfort layer. The one or more layers of the electronic device, such as the conductive and dielectric layers, are then deposited directly on the comfort layer and/or a separate second substrate. The second substrate optionally having the conductive layer and dielectric layer thereon is then coupled to, the comfort layer on the first substrate via lamination, fusing, or other methods. The first substrate on which the comfort layer is deposited on is then removed, such as by peeling, leaving the electric circuit assembly on the second substrate.

In yet another alternative embodiment (not shown), a comfort layer material is selectively deposited on a transfer substrate, the substrate comprising a web or sheet having an optional release layer. The comfort layer is cured so that it expands to form a well-formed comfort layer. The one or more layers of the electronic device, such as the conductive and dielectric layers, are then deposited directly on the comfort layer. A second, comfort layer is then selectively deposited on the first comfort layer and electronic device. The second comfort layer is cured to encapsulate the electronic device, such that the layers of the electronic device are sandwiched between the comfort layers. The substrate is then optionally removed, such that the finished assembly includes no substrate.

In yet another embodiment, the comfort layer is selectively deposited on a first portion of a substrate, such as a sheet. One or more layers of an electronic device are then selectively deposited or laminated to a second portion of the substrate, either directly on the substrate, or alternatively on a second comfort layer selectively deposited and cured on the second portion of the substrate. The substrate is then folded over to marry the one or more layers deposited on the second portion of the substrate to the comfort layer deposited on the first portion of the substrate (either cured or uncured). If not already cured, one or more layers of the assembly are cured such that the comfort layer(s) encapsulate the electronic device layers. At least the first portion of the substrate having the comfort layer thereon is removed; and in some embodiments, such as when the second comfort layer is present, the entire substrate is removed.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be formed or combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

What is claimed is:

1. A body-worn electronic circuit assembly having a buffering feature, the electronic circuit assembly comprising:
   a substrate;
   electronic circuitry including at least a conductive material deposited on a first side of the substrate; and
   a selectively deposited comfort layer encompassing at least a portion of the electronic circuitry,
   wherein the comfort layer provides the buffering feature such that substantially non-abrasive contact is made between the comfort layer and the skin of a wearer when the electronic circuit is placed on the wearer, wherein the portion of the electronic circuitry which is encompassed by the comfort layer does not contact the skin of the wearer, and wherein the substrate is not configured to be separated from the electronic circuitry.

2. A body-worn electronic circuit assembly having a buffering feature, the electronic circuit assembly comprising:
   a substrate;
   electronic circuitry including at least a conductive material deposited on a first side of the substrate;
   a selectively deposited comfort layer encompassing at least a portion of the electronic circuitry,
   wherein the comfort layer provides the buffering feature such that substantially non-abrasive contact is made when placed on a wearer of the electronic circuit assembly, and wherein the comfort layer comprises plastisol puff ink exhibiting a soft, sponge-like texture upon curing.

3. The body-worn electronic circuit assembly of claim 2, wherein the comfort layer is selectively deposited by printing, spray coating, or through a patterned or prepared mask.

4. The body-worn electronic circuit assembly of claim 3, wherein the comfort layer is deposited by a printing technique comprising gravure, waterless offset, direct image waterless offset, lithographic, intaglio, embossing, engraving, screen, rotary screen, silkscreen, letterpress, flatbed, digital printing, ink jet, drop on demand, xerographic, flexographic, aerosol, pad, dip-pen, or combinations thereof.

5. The body-worn electronic circuit assembly of claim 2, wherein the comfort layer exhibits electrically insulative properties such that the comfort layer provides electrical isolation for the encapsulated portions of the circuitry.

6. The body-worn electronic circuit assembly of claim 2, wherein the comfort layer provides mechanical protection to the encapsulated circuitry.

7. The body-worn electronic circuit assembly of claim 2, wherein the comfort layer is waterproof or water resistant such that the comfort layer protects the encapsulated circuitry from water moisture.

8. The body-worn electronic circuit assembly of claim 2, wherein the comfort layer is solvent-proof or solvent-resistant such that the comfort layer protects the encapsulated circuitry from chemical intrusion.

9. The body-worn electronic circuit assembly of claim 2, wherein the conductive material comprises a selectively deposited conductive layer formed from a material selected from the group consisting of silver, platinum, palladium, copper, nickel, gold, or aluminum or conductive polymer.

10. The body-worn electronic circuit assembly of claim 2, wherein the electronic circuitry further comprises a dielectric material selectively deposited and sandwiched between at least a portion of the conductive material and the comfort layer.

11. The body-worn electronic circuit assembly of claim 10, wherein the dielectric material comprises a vinyl or urethane resin.

12. The body-worn electronic circuit assembly of claim 2, wherein the substrate is flexible, and wherein the substrate, electronic circuitry and comfort layer are substantially free from memory folds upon flexure of the substrate.

13. The body-worn electronic circuit assembly of claim 2, further comprising a second selectively deposited comfort layer deposited over at least a portion of a second side of the substrate.

14. The body-worn electronic circuit assembly of claim 2, wherein the electronic circuitry is adapted and/or designed for monitoring nervous system signals, respiratory system signals, circulatory system signals, for providing electrical stimulation, electronic display, or any combination thereof.

15. The body-worn electronic circuit assembly of claim 2, wherein the assembly is incorporated into wearable smart clothes, hospital gowns, blankets, sheets, tents, mattress covers, towels, bibs, or pillow covers.

16. A flexible printed electronic to be worn on a body of a wearer, the flexible printed electronic comprising:
    a conductive layer which allows for the flow of electricity therethrough; and
    a comfort layer which covers or encapsulates at least a portion of the conductive layer, the comfort layer being a cured ink, the comfort layer configured to be positioned against the body of the wearer.

17. The flexible printed electronic of claim 16, wherein the cured ink is a plastisol ink having a puff additive.

18. The flexible printed electronic of claim 16, wherein the conductive layer is a base layer of the flexible printed electronic.

19. The flexible printed electronic of claim 16, wherein the conductive layer is formed of an electronic ink.

20. The flexible printed electronic of claim 16, further comprising a base layer, the conductive layer covers or encapsulates at least a portion of the base layer.

21. The flexible printed electronic of claim 20, wherein the base layer is fabric.

22. The flexible printed electronic of claim 21, wherein the fabric is provided in a piece of clothing.

23. The flexible printed electronic of claim 20, wherein the base layer is a substrate.

24. The flexible printed electronic of claim 23, wherein the flexible printed electronic is configured to be coupled to fabric provided in a piece of clothing.

25. A flexible printed electronic to be worn on a body of a wearer, the flexible printed electronic comprising:
    a conductive layer which allows for the flow of electricity therethrough;
    a dielectric layer which covers or encapsulates at least a portion of the conductive layer; and
    a comfort layer which covers or encapsulates at least a portion of the dielectric layer, the comfort layer being a cured ink, the comfort layer configured to be positioned against the body of the wearer.

26. The flexible printed electronic of claim 25, wherein the cured ink is a plastisol ink having a puff additive.

27. The flexible printed electronic of claim 25, wherein the conductive layer is a base layer of the flexible printed electronic.

28. The flexible printed electronic of claim 25, wherein the conductive layer is formed of an electronic ink.

29. The flexible printed electronic of claim 25, further comprising a base layer, the conductive layer covers or encapsulates at least a portion of the base layer.

30. The flexible printed electronic of claim 29, wherein the base layer is fabric.

31. The flexible printed electronic of claim 30, wherein the fabric is provided in a piece of clothing.

32. The flexible printed electronic of claim 29, wherein the base layer is a substrate.

33. The flexible printed electronic of claim 32, wherein the flexible printed electronic is configured to be coupled to fabric provided in a piece of clothing.

* * * * *